(12) United States Patent
Ho et al.

(10) Patent No.: US 9,341,363 B2
(45) Date of Patent: May 17, 2016

(54) DIGITAL READING DEVICE WITH COSMETIC FUNCTION

(71) Applicant: GCSOL Tech Co., Ltd., Taichung County (TW)

(72) Inventors: Fang-Chuan Ho, Hsinchu (TW); Jui-Fen Pai, Nantou County (TW)

(73) Assignee: GCSOL Tech Co., Ltd., Taichung (TW)

( * ) Notice: Subject to any disclaimer, the term of this patent is extended or adjusted under 35 U.S.C. 154(b) by 295 days.

(21) Appl. No.: 13/935,548

(22) Filed: Jul. 4, 2013

(65) Prior Publication Data

US 2014/0293597 A1    Oct. 2, 2014

(30) Foreign Application Priority Data

Apr. 2, 2013 (TW) .............................. 102111921 A

(51) Int. Cl.
| | |
|---|---|
| *F21V 33/00* | (2006.01) |
| *H01L 51/50* | (2006.01) |
| *H01L 27/32* | (2006.01) |
| *G06F 3/041* | (2006.01) |
| *A61N 5/06* | (2006.01) |

(52) U.S. Cl.
CPC ............ *F21V 33/0068* (2013.01); *G06F 3/041* (2013.01); *H01L 27/323* (2013.01); *H01L 51/50* (2013.01); *A61N 2005/0653* (2013.01); *A61N 2005/0663* (2013.01)

(58) Field of Classification Search
CPC .......... F21V 23/0485; F21Y 2105/008; G02B 27/021; G02B 27/024; G02F 1/0327; G02F 2001/133374; G02F 3/04; G02F 3/0412; G02F 3/0416; G02F 3/041; G09F 9/3023; G09G 3/3208; G09G 3/3258; G09G 3/342; H01L 27/3225; H01L 27/323; H01L 51/50; H05B 33/0896; A61N 2005/0653; A61N 2005/0663

USPC .................... 362/125, 227, 230, 231, 249.02, 362/97.1–97.4, 800, 600–634; 349/12, 16, 349/61, 63, 77, 78, 110; 345/173, 183

See application file for complete search history.

(56) References Cited

U.S. PATENT DOCUMENTS

| | | | |
|---|---|---|---|
| 2006/0066790 A1* | 3/2006 | Tanaka et al. ................ | 349/123 |
| 2010/0051973 A1* | 3/2010 | Kobayashi et al. ............ | 257/88 |
| 2010/0149223 A1* | 6/2010 | Betts-LaCroix .............. | 345/690 |

(Continued)

FOREIGN PATENT DOCUMENTS

EP    2493175 A1    8/2012

*Primary Examiner* — Evan Dzierzynski
*Assistant Examiner* — Zheng Song
(74) *Attorney, Agent, or Firm* — CKC & Partners Co., Ltd.

(57) ABSTRACT

A digital reading device with cosmetic function includes a base plate, a lighting panel, a driving unit and a transparent touch panel. The base plate includes a plurality of black units. The lighting panel is disposed on the base plate and includes as plurality of lighting units for emitting a green light. The driving unit is electrically connected to the lighting panel and the base plate, wherein the driving unit is for turning on or turning off each of the lighting units respectively. The transparent touch panel is disposed on the lighting panel for displaying a message composed of the black units. The message may also be white-colored on a green background color with various saturation levels whenever the lighting panel includes a plurality of displaying units, and each of the displaying units consists of two lighting units with complimentary colors.

10 Claims, 11 Drawing Sheets

(56) References Cited

U.S. PATENT DOCUMENTS

| | | | |
|---|---|---|---|
| 2012/0104938 A1* | 5/2012 | Chu et al. | 313/504 |
| 2012/0140492 A1* | 6/2012 | Alvarez | 362/382 |
| 2013/0194199 A1* | 8/2013 | Lynch et al. | 345/173 |
| 2013/0241841 A1* | 9/2013 | Orsley | 345/173 |
| 2014/0223803 A1* | 8/2014 | Hariyama et al. | 43/107 |
| 2015/0123569 A1* | 5/2015 | Knaapen et al. | 315/297 |

* cited by examiner

DIGITAL READING DEVICE WITH COSMETIC FUNCTION

RELATED APPLICATIONS

The application claims priority to Taiwan Application Serial Number 102111921, filed on Apr. 2, 2013, which is herein incorporated by reference.

BACKGROUND

1. Technical Field

The present disclosure relates to a digital reading device, especially relates to a digital reading device with cosmetic function.

2. Description of Related Art

With highly developments on the internet technology, transmission of electric messages is getting more important. Wide usages of the internet make it possible for obtaining a huge amount of messages in a short time thereby bring up the popularity of digital reader. A conventional digital reader usually utilizes a display device for displaying messages and an input device for interacting with a user. The display device is usually a liquid crystal panel.

On the other hand, an appearance of an individual is taking more weight in the modernization of the society. Skin is covering the human body not only protecting the body, but also determining the first impression of other people. Therefore, cosmetic methods in need have constantly been developed. Conventional cosmetic method is directed to smear cosmetic or a medicine on the skin directly. However, owing to the direct contact of the chemical component of the cosmetic or medicine with the skin, a variety of side effects may possibly occur. The chemical components of the cosmetic can be replaced with natural ones, however, there exists constrains on smearing cosmetic everywhere due to the limits on location, time and personal privacy.

Photo-cosmetic is a newly developed technology on skin care. The photo-cosmetic normally includes a process of irradiating a light to the skin first, and makes the energy of light be transferred into thermal or chemical energy after the light is absorbed by the skin, so as to lead to series reactions in the skin and to increase the hyperplasia and activation of the cell. Laser light and pulse light are commonly used as the light sources in the photo-cosmetic process.

Among the photo-cosmetic processes, the laser light or pulse light source may cause hazards on the skin surface or sensitive organs (e.g. eye) due to intense energy thereof. Photo-cosmetic may eliminate side effects of the conventional skin cosmetic, but the complicated operation procedure and the large equipment still lead to high cost and difficult operation for those who have needs of safe and convenient make-up or cosmetic at home.

SUMMARY

According to one aspect of the present disclosure, a digital reading device with cosmetic function is provided. The digital reading device with cosmetic function includes a base plate, a lighting panel, a driving unit and a transparent touch panel. The base plate includes a plurality of black units. The lighting panel is disposed on the base plate and includes a plurality of lighting, units for emitting a green light. The driving unit is electrically connected to the lighting panel and the base plate, wherein the driving unit is for turning on or turning off each of the lighting units respectively. The transparent touch panel is disposed on the lighting panel for displaying a message composed of the black units.

According to another aspect of the present disclosure, a digital reading device with cosmetic function is provided. The digital reading device with cosmetic function includes a base plate, a lighting panel, a driving, unit and a transparent touch panel. The base plate includes a plurality of black units. The lighting panel is disposed on the base plate and includes a plurality of displaying units, and each of the displaying units includes a first lighting unit and a second lighting unit. The first lighting unit emits a green light, and the second lighting unit emits a magenta light. The driving unit is electrically connected to the lighting panel and the base plate for adjusting a first intensity of each of the green lights and a second intensity of each of the magenta lights respectively. The transparent touch panel is disposed on the lighting panel for displaying a message formed by an arrangement of the black units or an arrangement of the displaying units. The green light of first lighting unit and the magenta light of the second lighting unit are mixed into a mixed light and passes through the transparent touch panel.

BRIEF DESCRIPTION OF THE DRAWINGS

The disclosure can be more fully understood by reading the following detailed description of the embodiment, with reference made to the accompanying drawings as follows.

DETAILED DESCRIPTION

The present disclosure provides a digital reading device with cosmetic function. The digital reading device with cosmetic function is not only for displaying electric messages but also emitting a light with specified wavelength region to the user. Therefore, a cosmetic effect on the user's skin will be obtained while reading the messages. Furthermore, the lighting panel of the digital reading device with cosmetic function utilizes organic light emitting diodes, so that a proper light intensity will be obtained for preventing hazards to the user's skin or eye, etc.

Figure 1:
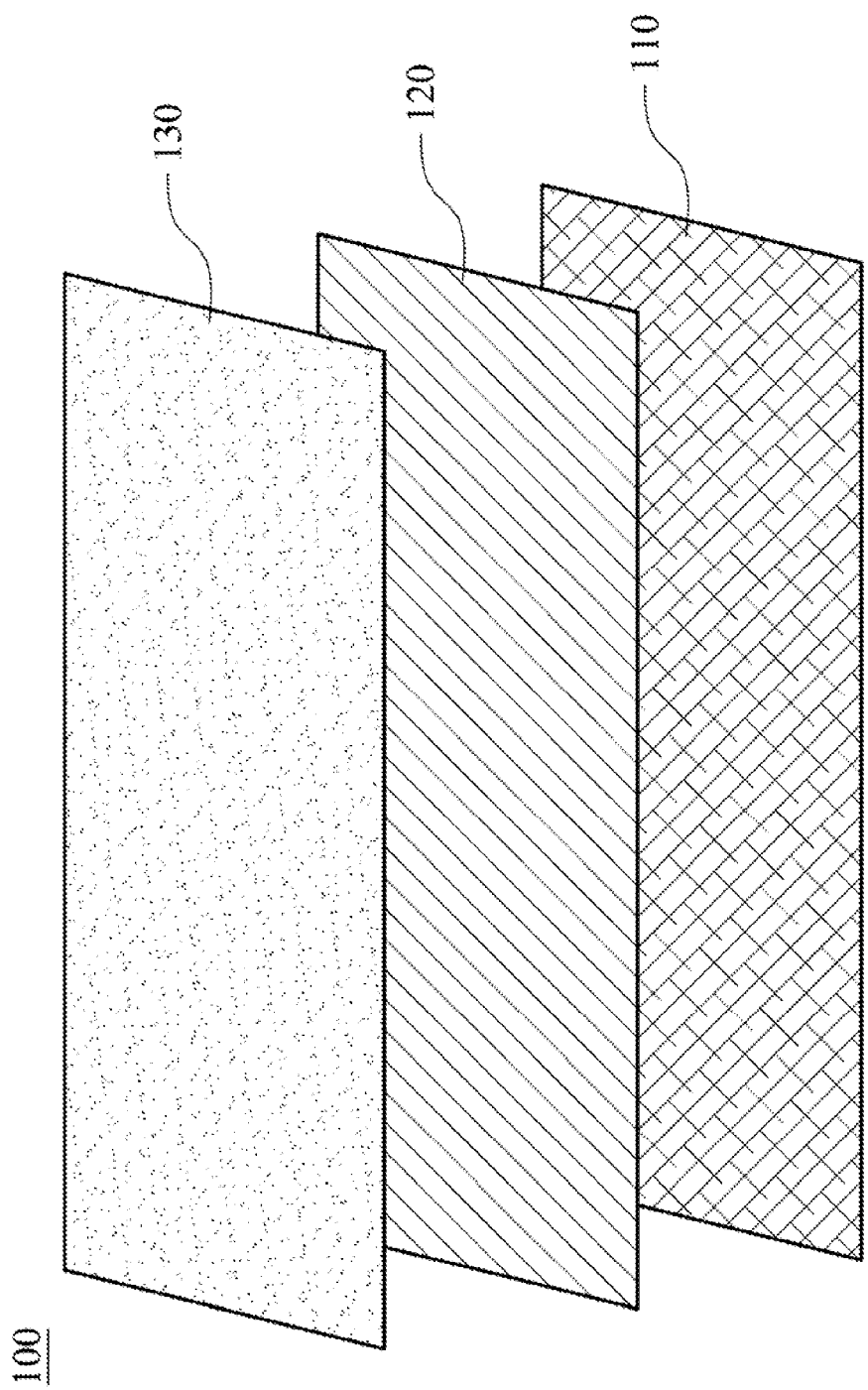
FIG. 1 shows a schematic view of a digital reading device with cosmetic function according to one embodiment of the present disclosure.

FIG. 1 shows a schematic view of a digital reading device with cosmetic function 100 according to one embodiment of the present disclosure. The digital reading device with cosmetic function 100 includes a base plate 110, a lighting panel 120 and a transparent touch panel 130. The lighting panel 120 is disposed on the base plate 110, and the transparent touch panel 130 is disposed on the lighting panel 120. A light is emitted from the lighting panel 120 and passes through the transparent touch panel 130 for displaying a message. Further, the light with a specific wavelength provides a cosmetic effect on the user's skin.

Figure 2A:
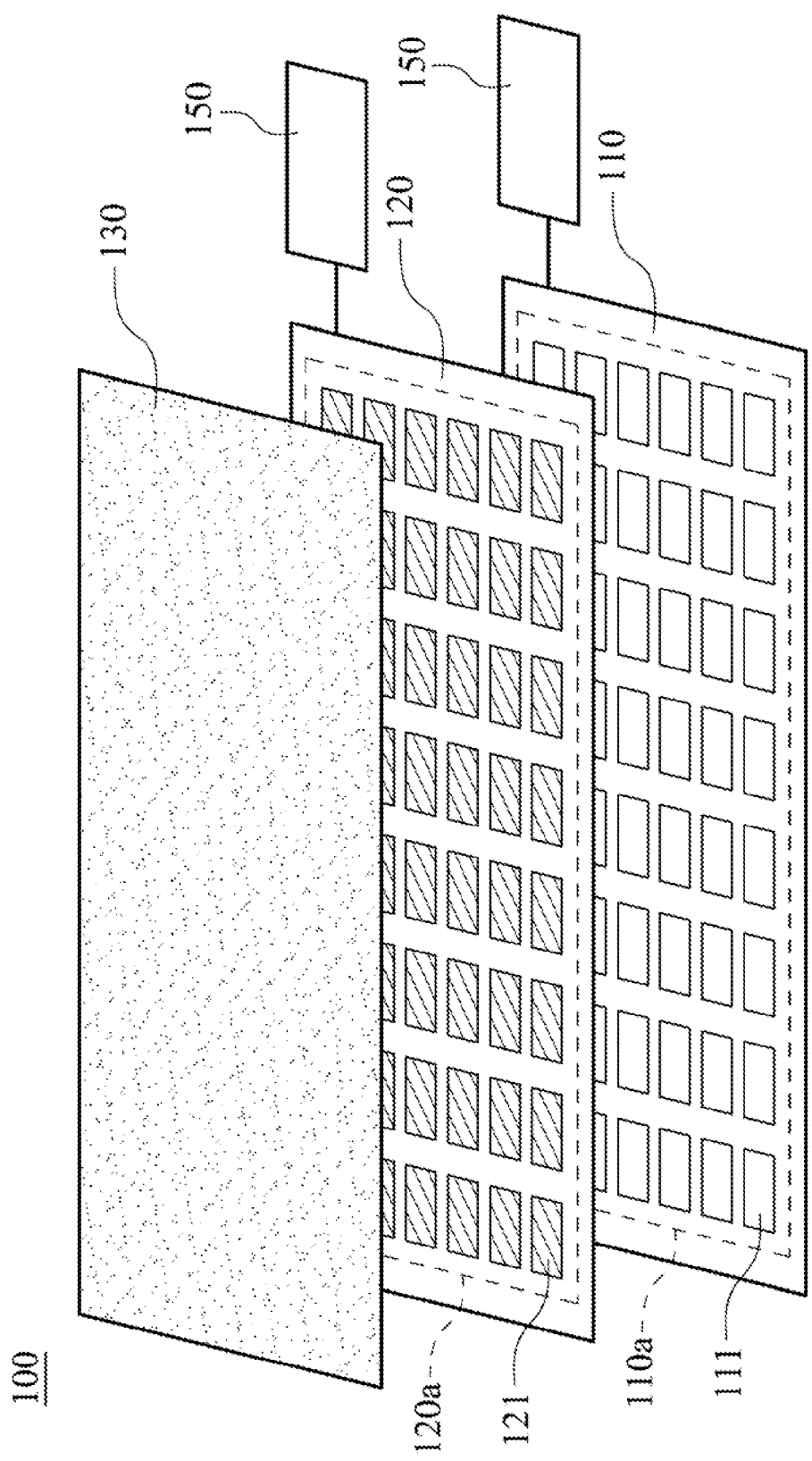
FIG. 2A shows a schematic view of the lighting units of the lighting panel according to the embodiment of FIG. 1.

FIG. 2A shows a schematic view of the lighting units 121 of the lighting panel 120 according to the embodiment of FIG. 1. A plurality of lighting units 121 is disposed on the lighting panel 120. Each of the lighting units 121 emits a green light, and a green lighting matrix 120a is formed. A plurality of black units 111 is disposed on the base plate 110, and a black matrix 110a is formed. A driving unit 150 is electrically connected with the base plate 110 and the lighting panel 120 for turning on or of each of the lighting units 121. Driving modes of the driving unit 150 can be a passive driving mode or an active driving mode. A position of each of the lighting units 121 on the green lighting matrix 120a is corresponded to a position of each of the black units 111 on the black matrix 110a.

Figure 2B:
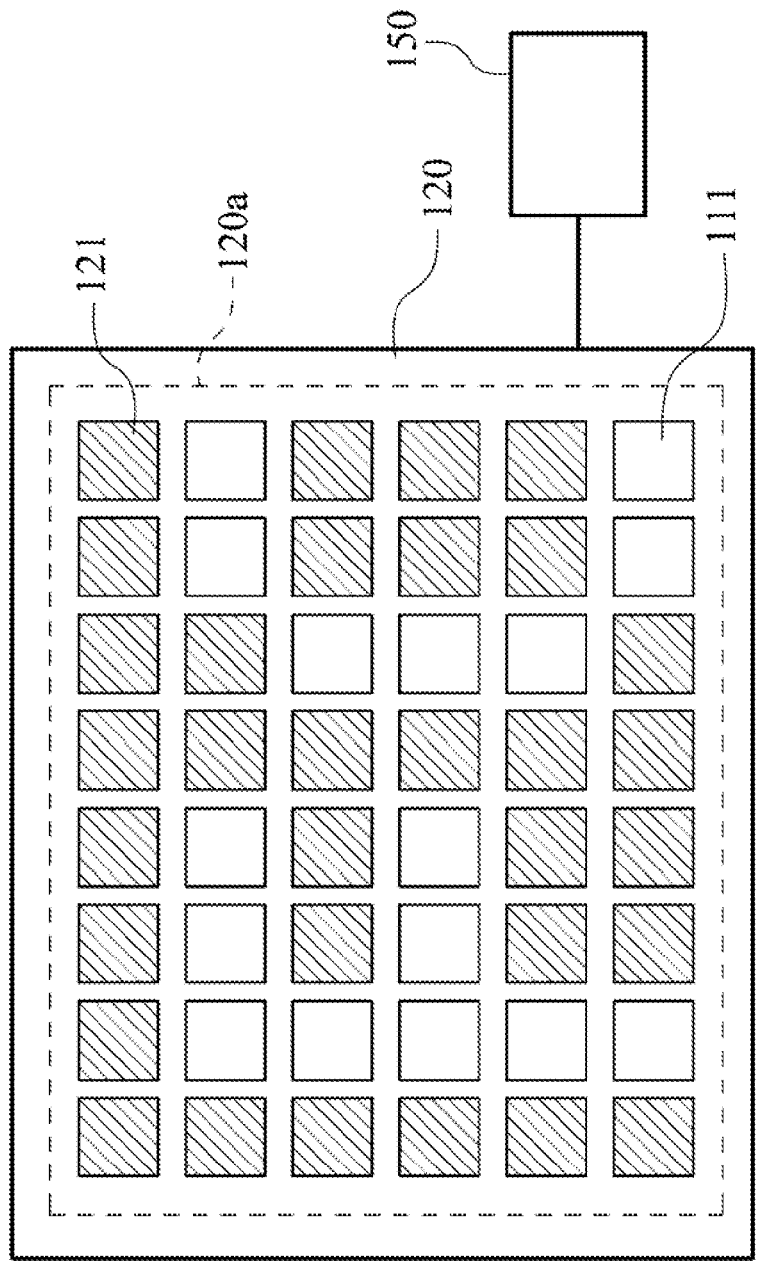
FIG. 2B is a top-side view showing the arrangement of the lighting units of FIG. 2A.

FIG. 2B is a topside view showing the arrangement of the lighting units 121 of FIG. 2A. When one of the lighting units 121 is turned off by the driving unit 150, the black unit 111 corresponding to the lighting, units 121 is exposed. Therefore, by turning on or turning off each of the lighting units 121 can control each of the black units 111 being exposed or blocked, thus a text or a picture can be formed by the arrangement of the black units 111. In FIG. 1, the lighting panel 120 is disposed on the base plate 110, and the transparent touch panel 130 is disposed on the lighting panel 120. That is, the user sees the message (the text or the picture) which arranged by the black units 111 through the transparent touch panel 130.

In the embodiment of FIG. 1, each of the lighting units 121 emits a green light, so that the user can see a black message under a green background light, wherein the green background light provides by the lighting units 141 which are not be turned off. The lighting unit 121 can be an organic light emitting diode, and the green light emitted by the lighting unit 121 is selected, as a specified wavelength region, such as 521±10 nm, which is suitable for skin anti-ager and rejuvenation. By the characteristic of organic light emitting diode, the green light emitted from the lighting unit 121 is proper to be the green background light, wherein the green light has a proper energy (e.g. smaller than 1 mW/cm$^2$ at 10 cm away from the lighting panel 120), a uniform intensity and an excellent CRI (Color Rendering Index). Therefore, in the time that the user reads a message formed by the arrangement of the black units 111, the lighting units 121 emit a green light with a specified wavelength region to the user's skin, thus a cosmetic effect is obtained.

Figure 3A:
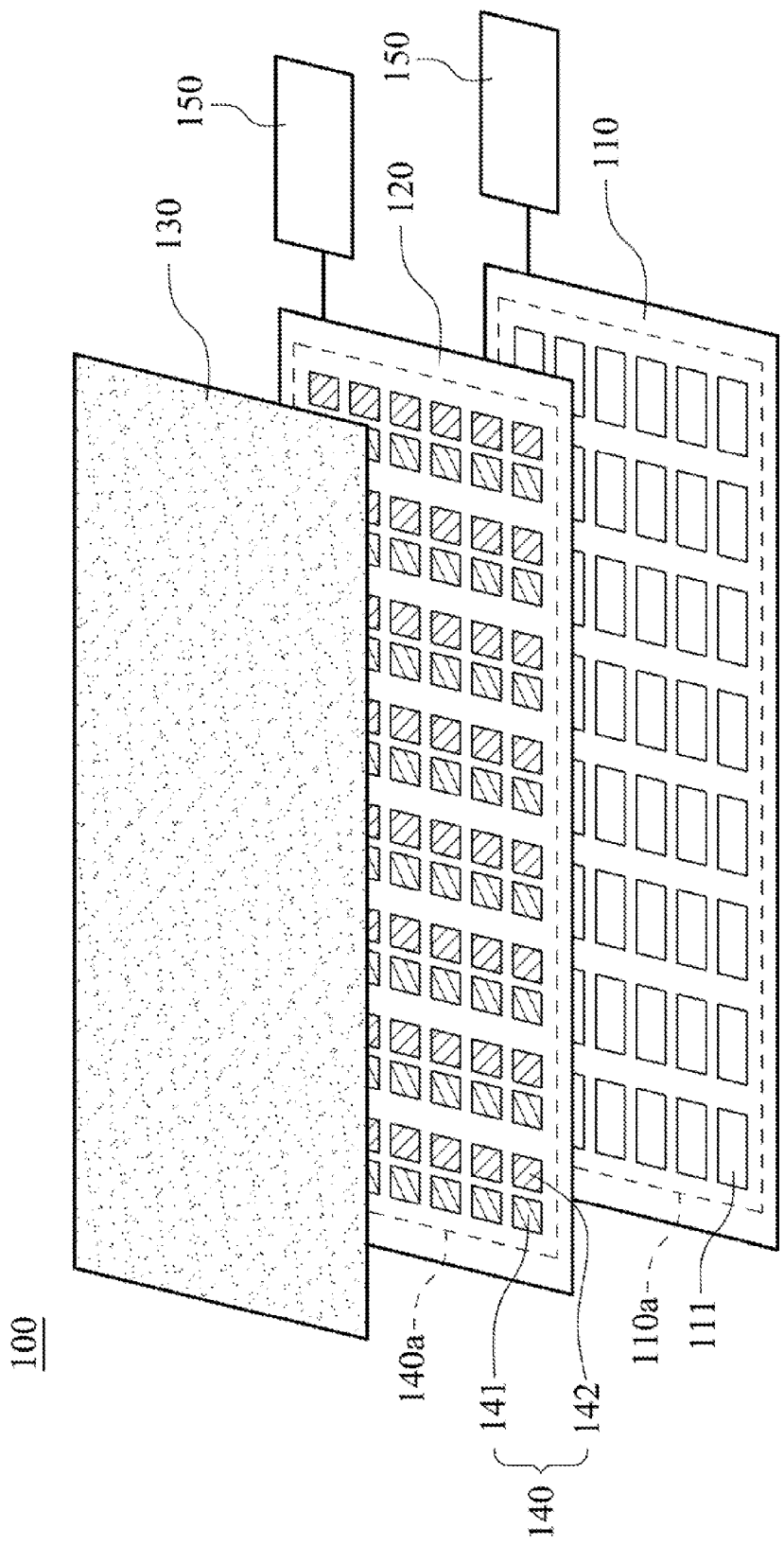
FIG. 3A shows a schematic view of the displaying units according to another embodiment of FIG. 1.

FIG. 3A shows a schematic view of the displaying units 140 according to another embodiment of FIG. 1. In FIG. 3A, the lighting panel 120 includes a plurality of displaying units 140, and each of the displaying units 140 includes a first lighting unit 141 and a second lighting unit 142. The first lighting unit 141 emits a green light, and the second lighting unit 142 emits a magenta light, and an emitted light of each of the displaying units 140 is a mixed light which is mixed by the first lighting unit 141 and the second lighting unit 142. The displaying units 140 are arranged to form a main lighting matrix 140a, and the black units 111 are arranged to form a black matrix 110a. A driving unit 150 is electrically connected with the base plate 110 and the lighting panel 120 for adjusting a first intensity of the green light of the first lighting units 141 and a second intensity of the magenta light of the second lighting units 142. A position of each of the displaying units 140 on the main lighting matrix 140a is corresponded to a position of each of the black unit 111 on the black matrix 110a.

Figure 3B:
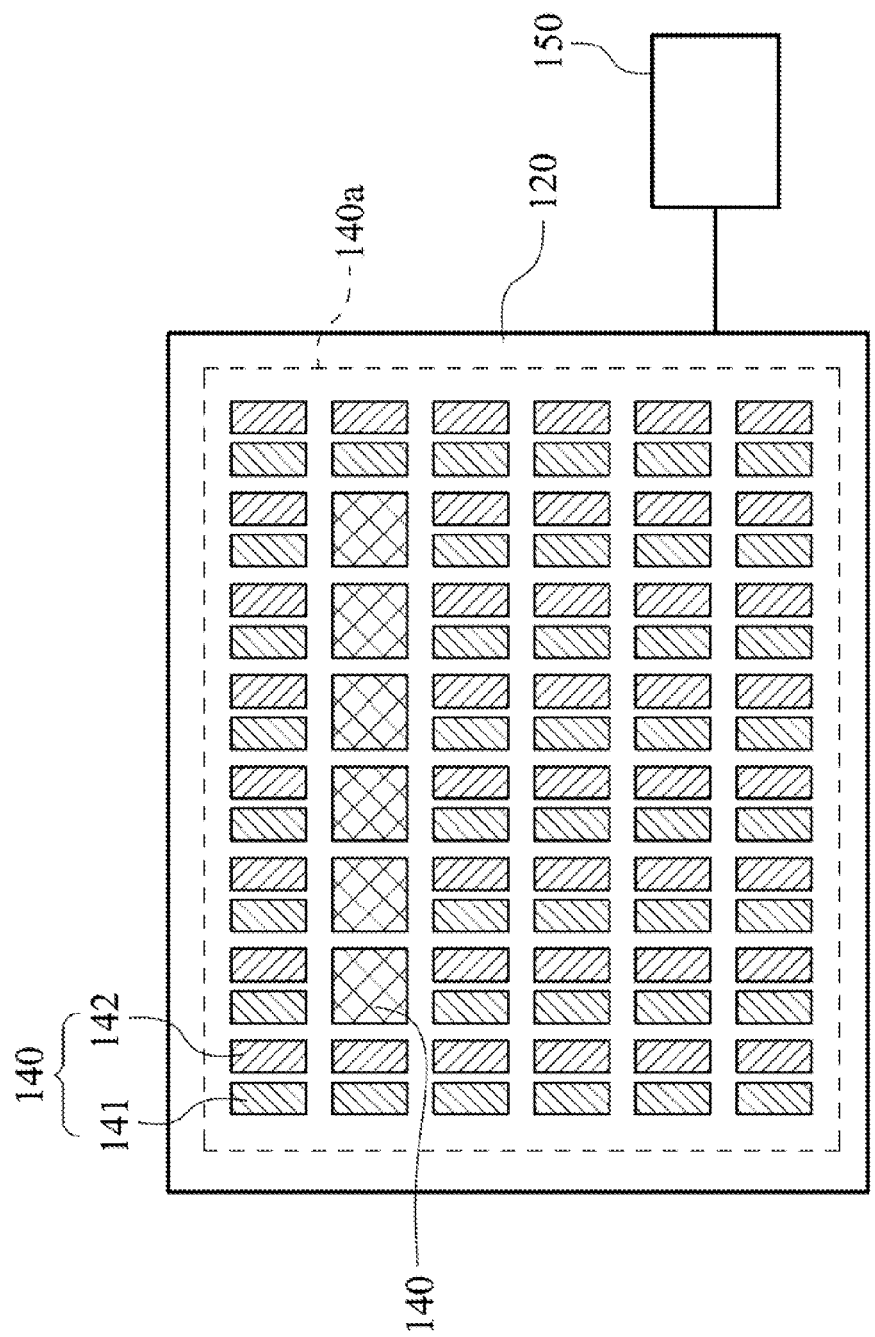
FIG. 3B is a top-side view showing the displaying units according to the embodiment of FIG. 3A.
Figure 3C:
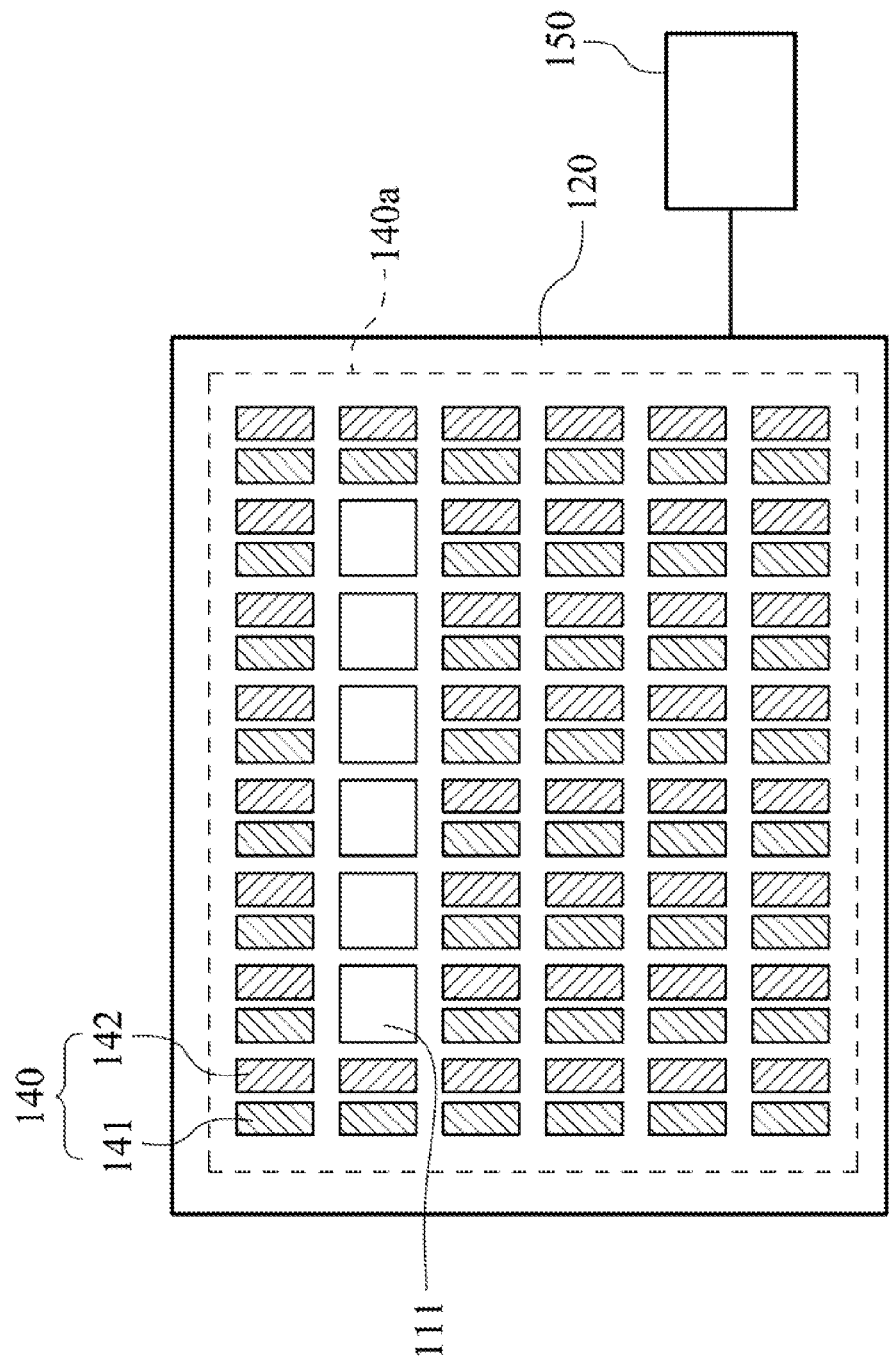
FIG. 3C is a top-side view showing the displaying units and the black unit according to the embodiment of FIG. 3A.

FIG. 3B is a top-side view showing the displaying units 140 according to the embodiment of FIG. 3A; and FIG. 3C is a top-side view showing the displaying units 140 and the black unit 111 according to the embodiment of FIG. 3A. The user can see through the transparent touch panel 130, and a message (text or picture) is displayed by the arrangement of the black units 111 on the base plate 110, or by the arrangement of the displaying units 140 on the lighting panel 120. In FIG. 3B, the mixed light emitted from the displaying units 140 can be a white light for forming a message, wherein the white light is formed by a mixing of the green light with the first intensity of the first lighting unit 141 and the magenta light with the second intensity of the second lighting unit 142. Moreover, the mixed light of the displaying units 140 is also used for forming a green background light with cosmetic effect. The green background light is formed by the mixed light emitted from at least one of the displaying units 140, wherein the first intensity of the green light of the first lighting unit 141 is increased to a full intensity (that is, 100% intensity) and the second intensity of the magenta light of the second lighting unit 142 is decreased by the driving unit 150, thus the green background color with different saturation levels is formed. In the embodiment, two different message colors can be selected under a green background light. First, in FIG. 3C, the first lighting units 141 and the second lighting units 142 of parts of the displaying units 140 are turned off, so that the corresponding black units 111 are exposed. That is, the message is displayed by the exposed black units 111. According to the arrangement of the black units 111, the message can be a black-colored text or a black-colored picture. Second, in FIG. 3B, the message is displayed by the mixed light from the displaying unit 140, which is a mixing of the lighting unit 141 with the first intensity and the second lighting units 142 with the second intensity, and the mixed light is a white light. Therefore, the arrangement of the displaying units 140 forms a white-colored text or a white-colored picture. Thus, a user can read a black-colored message formed by the arrangement of the black units 111 or a white-colored message formed by the displaying unit 140, and the green background light with various saturation color levels can be emitted to the user's skin for providing different cosmetic effects during reading.

In the above embodiment, the lighting panel 120 is electrically connected to the driving unit 150, and each of the first lighting unit 141 and each of the second lighting unit 142 of the displaying units 140 can be adjusted independently. Therefore, different power ratios can be used for adjusting the first intensity of the green light of the first lighting unit 141 and the second intensity of the magenta light of the second lighting unit 142 respectively. By such adjustment, the green background light with various saturation color levels can be obtained and various cosmetic effects can be provided. Each of the first lighting unit 141 and the second lighting unit 142 is a transparent organic light emitting diode. With the characteristic of organic light emitting diode, the lighting panel 120 can emit a green background light with a proper energy (e.g. smaller than 1 mW/cm$^2$ at 10 cm away from the lighting panel 120), a uniform intensity and an excellent CRI (Color Rendering Index).

In the following sections, various examples are performed to show different wavelength-intensity spectrums of mixing of the green light with the first intensity of the first lighting unit 141 and the magenta light with the second intensity of the second lighting unit 142. Therefore different saturation color levels of the green background light of the digital reading device with cosmetic function 100 can be achieved.

Figures 4A, 4B:
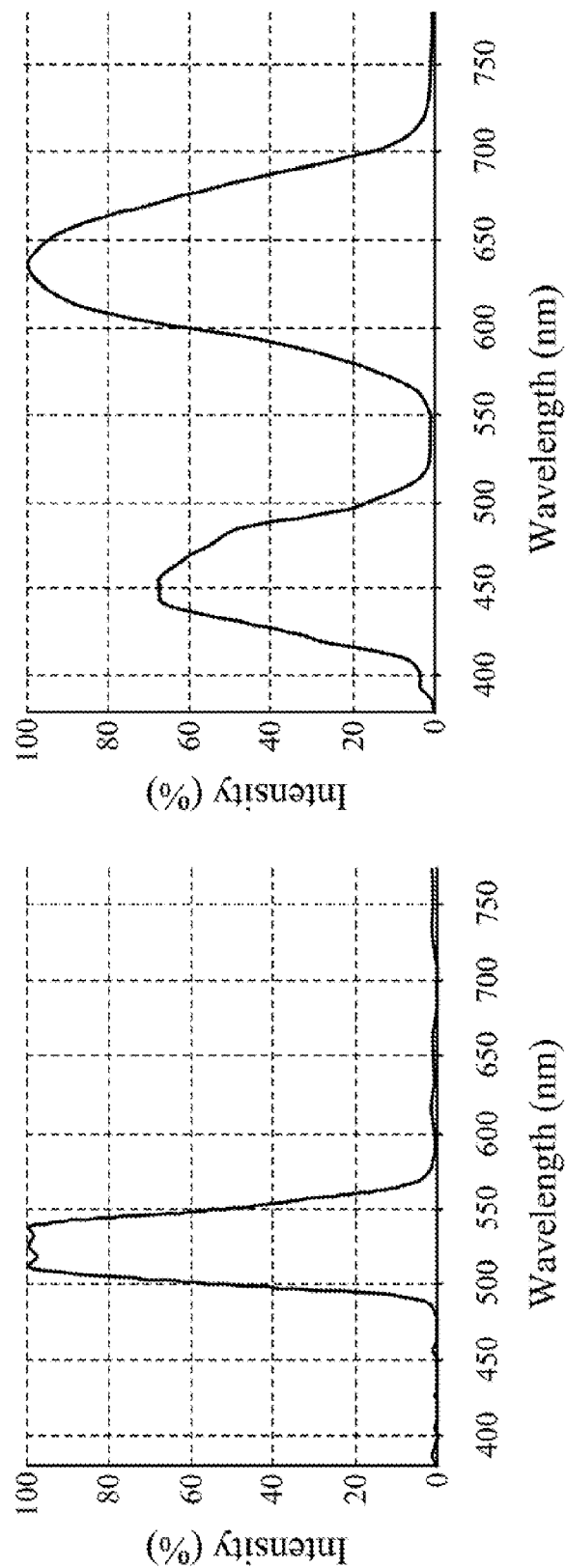
FIG. 4A illustrates a wavelength-intensity spectrum of the green light of the first lighting units of FIG. 3A.
FIG. 4B illustrates a wavelength-intensity spectrum of the magenta light of the second lighting units of FIG. 3A.
Figure 4C:
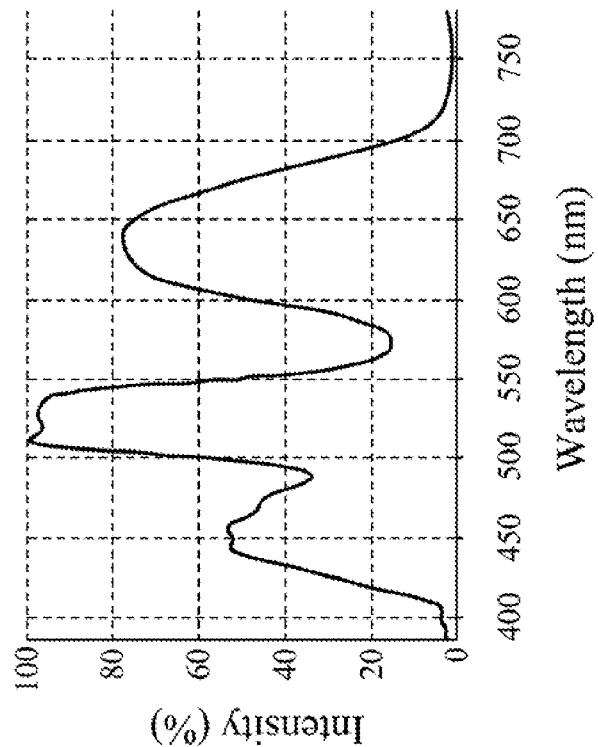
FIG. 4C illustrates a wavelength-intensity spectrum of the mixed light from the green light of FIG. 4A and the magenta light of FIG. 4B.

FIG. 4A illustrates a wavelength-intensity spectrum of the green light of the first lighting, units 141 of FIG. 3A; FIG. 4B illustrates a wavelength-intensity spectrum of the magenta light of the second lighting units 142 of FIG. 3A; and FIG. 4C illustrates a wavelength-intensity spectrum of the mixed light from the green light of FIG. 4A and the magenta light of FIG. 48. In FIG. 4A, the first lighting unit 141 emits a green light with a single wavelength region; the peak position is located at 527±10 nm. In FIG. 4B, the second lighting unit 142 emits a magenta light, and the magenta light is a combination of a blue light and a red light. The peak position of the blue light is located at 450±10 nm, and the peak position of the red light is located at 630±10 nm. In FIG. 4C, a white light spectrum is showed by the combination of the green light emitted from the first lighting unit 141 of FIG. 4A and the magenta light emitted from the second lighting unit 142 of FIG. 4B.

Figure 4D:
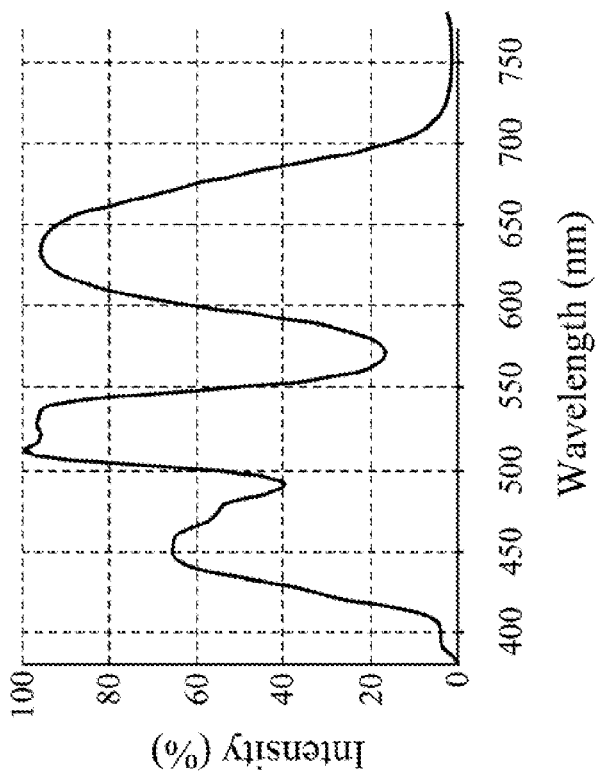
FIG. 4D illustrates a wavelength-intensity spectrum of the mixed light from the displaying unit of another example of FIG. 3A.
Figure 4E:
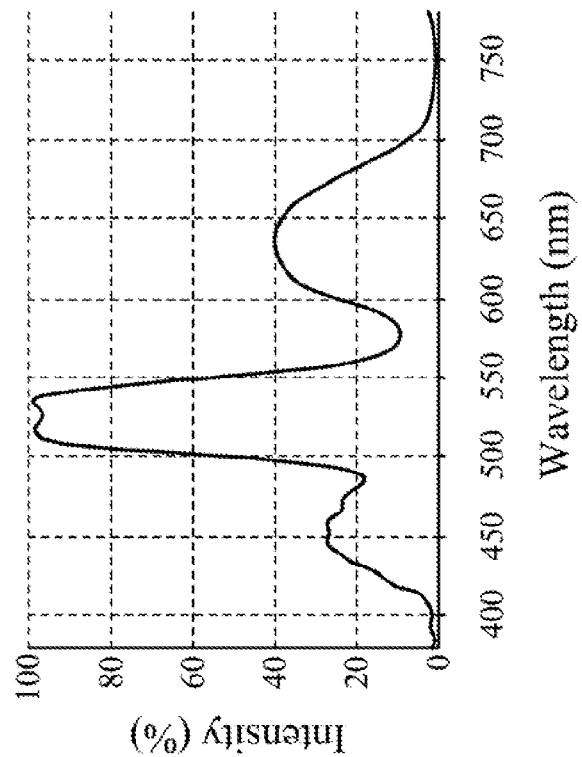
FIG. 4E illustrates a wavelength-intensity spectrum of the mixed light from the displaying unit of still another example of FIG. 3A.
Figure 4F:
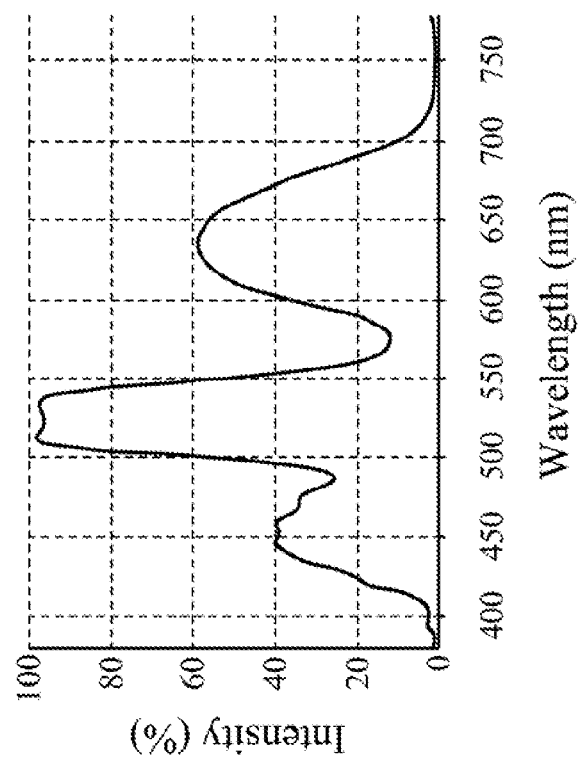
FIG. 4F illustrates a wavelength-intensity spectrum of the mixed light from the displaying unit of further another example of FIG. 3A.
Figure 4H:
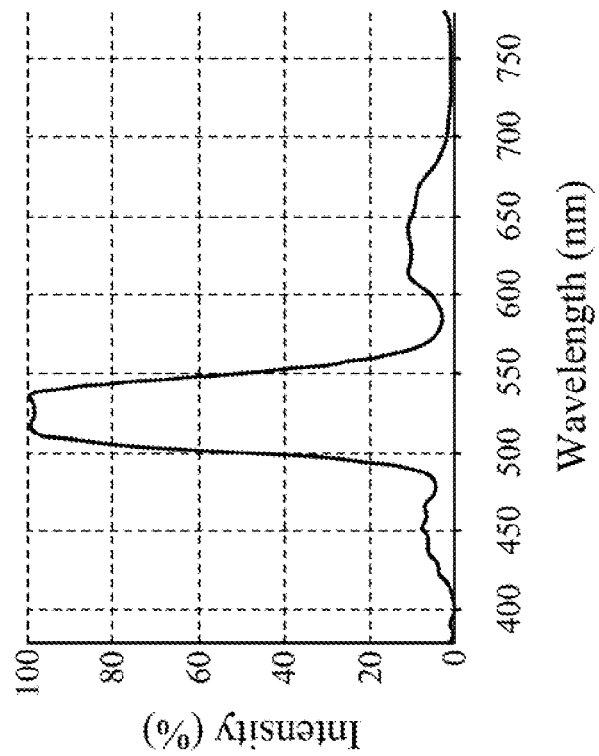
FIG. 4H illustrates a wavelength-intensity spectrum of the mixed light from the displaying unit of another example of FIG. 3A.
Figure 4G:
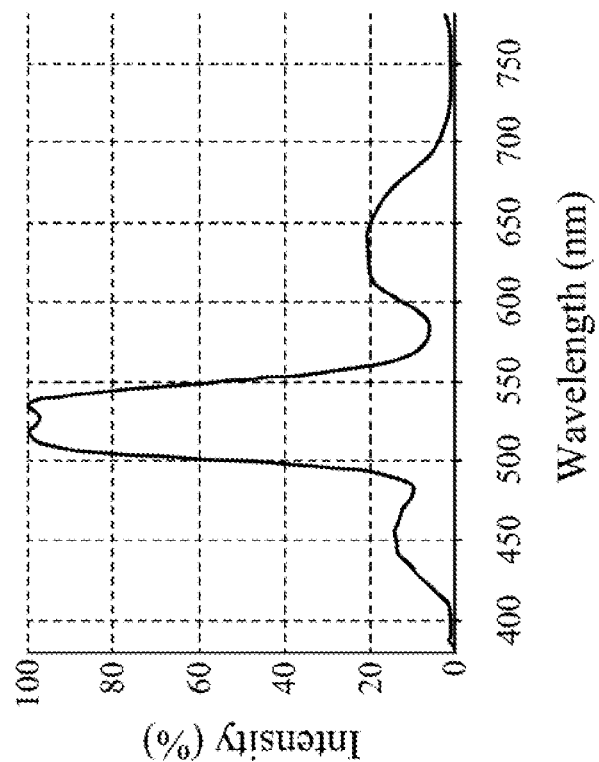
FIG. 4G illustrates a wavelength-intensity spectrum of the mixed light from the displaying unit of another example of FIG. 3A.

FIGS. 4D-4H illustrate wavelength-intensity spectrums of the mixed light from the displaying unit 140 of different examples of FIG. 3A. In FIG. 4D, the mixed light is mixed by the green light of the first lighting unit 141 with 100% intensity and the magenta light of the second lighting unit 142 with 80% intensity. In FIG. 4E, the mixed light is mixed by the green light of the first lighting unit 141 with 100% intensity and the magenta light of the second lighting unit 142 with 60% intensity. In FIG. 4F, the mixed light is mixed by the green light of the first lighting unit 141 with 100% intensity and the magenta light of the second lighting unit 142 with 40% intensity. In FIG. 4G, the mixed light is mixed by the green light of the first lighting unit 141 with 100% intensity and the magenta light of the second lighting unit 142 with 20% intensity. In FIG. 4H, the mixed light is mixed by the green light of the first lighting unit 141 with 100% intensity and the magenta light of the second lighting unit 142 with 10% intensity.

From FIG. 4D to FIG. 4H, it is shown that various wavelength regions are obtained by mixing of the green light with full first intensity of the first lighting unit 141 and the magenta light with various second intensity of the second lighting unit 142. Therefore, by adjusting the second lighting unit 142, different saturation color levels of the green background light can be obtained for achieving different cosmetic effects.

Figure 5:
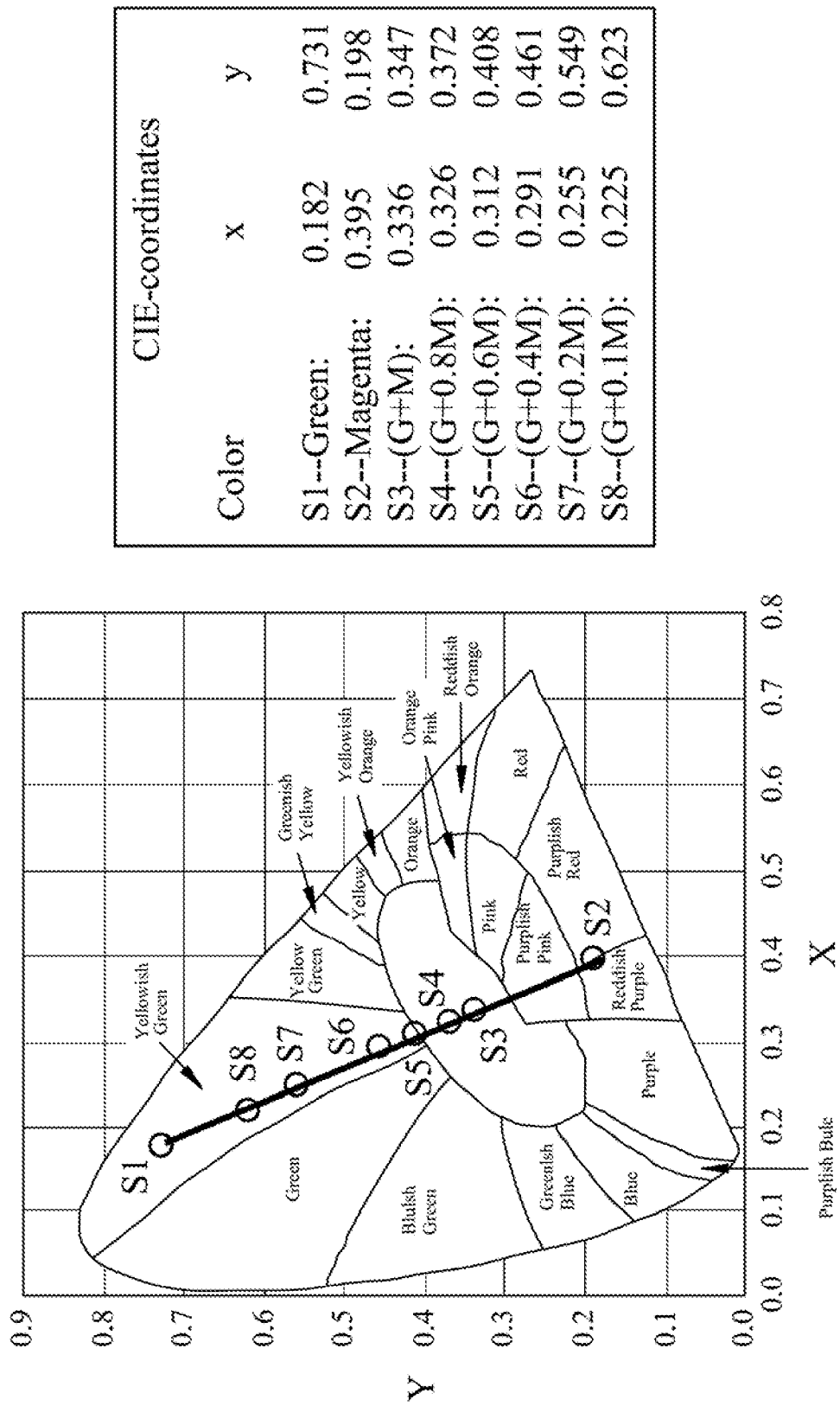
FIG. 5 is a CIE chart showing a combination of the 100% power driven first lighting units and different power driven second lighting units.

FIG. 5 is a CIE chart showing a combination of different first intensity of the green light of the first lighting units 141 and various second intensity of the magenta light of the second lighting units 42. S1 to S8 represent different color coordinate values in a CIE chart corresponded to different light intensity of the first lighting unit 141 and the second lighting unit 142. The corresponded color coordinate values are shown in table 1.

TABLE 1

| | Condition | | | |
|---|---|---|---|---|
| Position | Intensity of the first lighting unit | Intensity of the second lighting unit | CIE Color Coordinate X | CIE Color Coordinate Y |
| S1 | 100% | 0% | 0.182 | 0.731 |
| S2 | 0% | 100% | 0.395 | 0.198 |
| S3 | 100% | 100% | 0.336 | 0.347 |
| S4 | 100% | 80% | 0.326 | 0.372 |
| S5 | 100% | 60% | 0.312 | 0.408 |
| S6 | 100% | 40% | 0.291 | 0.461 |
| S7 | 100% | 20% | 0.255 | 0.549 |
| S8 | 100% | 10% | 0.225 | 0.623 |

From table 1, it is known that different color coordinates in FIG. 5 can be controlled by adjusting different light intensity of the first lighting unit 141 and the second lighting unit 142 respectively, which means that the green background light of the digital reading device with cosmetic function 100 can have various wavelength regions, thus various cosmetic effects can be obtained.

To sum up, the disclosure provides a digital reading device with cosmetic function. By different arrangements of the lighting units, a green background light with specified wavelength regions can be emitted to a user for providing a comfortable reading environment. At the same time, the specified green wavelength regions can provide various cosmetic effects to the user's skin. Furthermore, the compact size of the digital reading device with cosmetic function (7.5 inches 10 inches) makes it thin and portable. Therefore, the digital reading device with cosmetic function in the disclosure can be carried everywhere so as to perform photo-based cosmetic everywhere.

It will be apparent to those skilled in the art that various modifications and variations can be made to the structure of the present disclosure without departing from the scope or spirit of the disci tire. In view of the foregoing, it is intended that the present disclosure covers modifications and variations of this disclosure provided they fall within the scope of the following claims.

What is claimed is:

1. A digital reading device with cosmetic function, comprising:
   a base plate having a plurality of black units;
   a lighting panel disposed on the base plate and comprising a plurality of lighting units for emitting a green light, wherein a position of each of the lighting units is corresponded to a position of each of the black units;
   a driving unit electrically connected to the lighting panel and the base plate, wherein the driving unit is for turning on or turning off each of the lighting units respectively; and
   a transparent touch panel disposed on the lighting panel for displaying a message composed of the black units;
   wherein,
   each of the black units is originally sheltered by each of the lighting units; when one of the lighting units is turned off by the driving unit, the black unit sheltered by the lighting unit is exposed, and the message is a text or a picture formed by an arrangement of each of the exposed black units;

wherein the lighting units turned on and emit the green lights are acted as a green background color with cosmetic function of the digital reading device.

2. The digital reading device with cosmetic function of claim 1, wherein each of the lighting units is an organic light emitting diode.

3. The digital reading device with cosmetic function of claim 1, wherein a wavelength of the green light emitted from the lighting panel is from 517 nm to 537 nm.

4. The digital reading device with cosmetic function of claim 1, wherein the lighting panel is sized from 7.5-inch to 10-inch.

5. The digital reading device with cosmetic function of claim 1, wherein a resolution of the lighting panel is greater than 300 pixels per inch.

6. The digital reading device with cosmetic function of claim 1, wherein a light intensity of the lighting panel is smaller than 1 mW/cm$^2$ at 10 cm away from the lighting panel.

7. The digital reading device with cosmetic function of claim 1, wherein a driving mode of the driving unit is a passive driving mode or an active driving mode.

8. A digital reading device with cosmetic function, comprising:
   a base plate having a plurality of black units;
   a lighting panel disposed on the base plate and comprising;
      a plurality of displaying units, each of the displaying units comprising:
         a first lighting unit for emitting a given light; and
         a second lighting unit for emitting a magenta light;
      wherein a position of each of the displaying units is corresponded to a position of each of the black units;
   a driving unit electrically connected to the lighting panel and the base plate for adjusting, a first intensity of each of the green lights and a second intensity of each of the magenta lights respectively; and
   a transparent touch panel disposed on the lighting panel for displaying a message formed by the black units or the displaying units;
   wherein the green light from the first lighting units and the magenta light from the second lighting units are mixed into a mixed light and passes through the transparent touch panel;
   wherein,
   each of the black units is originally sheltered by each of the displaying units;
   when one of the displaying units is turned off by the driving unit, the black unit sheltered by the displaying unit is exposed, the message is a black text or a black picture formed by an arrangement of a plurality of exposed black units, and a green background color with different saturation levels is formed by the displaying units that are turned on, wherein in each of the displaying units that forms the green background color, the first intensity of the green light of the first lighting unit is gradually increased to full intensity and the second intensity of the magenta light of the second lighting unit is gradually decreased to zero intensity by the driving unit thereby forming different saturation levels of the green background color:
   when one of the displaying units is turned on by the driving unit, and the first intensity of the first lighting unit and the second intensity or the second lighting unit are both in 100% ratio, the mixed light is a white light, and the message is a white text or a white picture formed by an arrangement of a plurality of displaying units which emits white light; and a green background color with different saturation levels is formed by the displaying units that the first intensity of the first lighting unit thereof and the second intensity of the second lighting unit thereof are not in 100% ratio, wherein in each of the displaying units that forms the green background color, the first intensity of the green light of the first lighting unit is gradually increased to full intensity and the second intensity of the magenta light of the second lighting unit is gradually decreased to zero Intensity by the driving unit thereby forming different saturation levels of the green background color.

9. The digital reading device with cosmetic function of claim 8, wherein each of the first lighting units is an organic light emitting diode.

10. The digital reading device with cosmetic function of claim 8, wherein each of the second lighting units is an organic light emitting diode.

* * * * *